(12) United States Patent
Li et al.

(10) Patent No.: US 8,592,651 B2
(45) Date of Patent: Nov. 26, 2013

(54) ANTIMICROBIAL PEPTIDES AND USES THEREOF

(75) Inventors: Zhijian T. Li, Altamonte Springs, FL (US); Dennis J. Gray, Howey-in-the-Hills, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 866 days.

(21) Appl. No.: 11/922,048

(22) PCT Filed: Jun. 13, 2006

(86) PCT No.: PCT/US2006/022935
§ 371 (c)(1),
(2), (4) Date: Oct. 6, 2009

(87) PCT Pub. No.: WO2006/138276
PCT Pub. Date: Dec. 28, 2006

(65) Prior Publication Data
US 2010/0024068 A1    Jan. 28, 2010

Related U.S. Application Data

(60) Provisional application No. 60/689,937, filed on Jun. 13, 2005.

(51) Int. Cl.
*A01H 5/00* (2006.01)
*A01H 1/06* (2006.01)
*C12N 15/82* (2006.01)
*C07H 21/04* (2006.01)
*A01N 63/00* (2006.01)

(52) U.S. Cl.
USPC ......... 800/301; 800/279; 536/23.4; 424/93.1; 424/93.7

(58) Field of Classification Search
None
See application file for complete search history.

(56) References Cited

U.S. PATENT DOCUMENTS

| | | | |
|---|---|---|---|
| 5,593,866 | A | 1/1997 | Hancock et al. |
| 5,707,855 | A | 1/1998 | Hancock et al. |
| 6,232,528 | B1 * | 5/2001 | Scorza et al. ................. 800/279 |
| 6,288,212 | B1 | 9/2001 | Hancock et al. |
| 6,818,407 | B2 | 11/2004 | Hancock et al. |
| 2004/0177404 | A1 | 9/2004 | Li et al. |

FOREIGN PATENT DOCUMENTS

WO    WO 01/36647    5/2001

OTHER PUBLICATIONS

Andersons, D. et al. "Biologically active and amidated cecropin produced in a baculovirus expression system from a fusion construct containing the antibody-binding part of protein A" *Biochem. J.*, 1991, pp. 219-224, vol. 280.
Boman, H. G. et al. "Antibacterial and antimalarial properties of peptides that are cecropin-melittin hybrids" *FEBS*, Dec. 1989, pp. 103-106, vol. 259, No. 1.
Boman, H. G. et al. "Cell-Free Immunity in Insects" *Ann. Rev. Microbiol.*, 1987, pp. 103-126, vol. 41.
Christensen, B, et al. "Channel-forming properties of cecropins and related model compounds incorporated into planar lipid membranes" *Proc. Natl. Acad. Sci.*, Jul. 1988, pp. 5072-5076, vol. 85.
Florack, D. et al. "Expression of giant silkmoth cecropin B genes in tobacco" *Transgenic Res.*, 1995, 4(2):132-141, abstract only.
Gough, M. et al. "Antiendotoxin Activity of Cationic Peptide Antimicrobial Agents" *Infection and Immunity*, Dec. 1996, pp. 4922-4927, vol. 64, No. 12.
Habermann, E. "Bee and Wasp Venoms" *Science*, Jul. 28, 1972, pp. 314-322, vol. 177, No. 4046.
Hightower, R. et al. "The expression of cecropin peptide in transgenic tobacco does not confer resistance to *Pseudomonas syringae* pv *tabaci*" *Plant Cell Reports*, 1994, 13(5):295-299, abstract only.
Lee, J. et al. "Antibacterial peptides from pig intestine: Isolation of a mammalian cecropin" *Proc. Natl. Acad. Sci.*, Dec. 1989, pp. 9159-9162, vol. 86.
Li, Z. T. et al. "Bi-directional duplex promoters with duplicated enhancers significantly increase transgene expression in grape and tobacco" *Transgenic Research*, 2004, pp. 143-154, vol. 13.
Li, Z. et al. "Expression of a bifunctional green fluorescent protein (GFP) fusion marker under the control of three constitutive promoters and enhanced derivatives in transgenic grape (*Vitis vinifera*)" *Plant Science*, 2001, pp. 877-887, vol. 160.
Osusky, M, et al. "Transgenic plants expressing cationic peptide chimeras exhibit broad-spectrum resistance to phytopathogens" *Nature Biotechnology*, Nov. 2000, pp. 1162-1166, vol. 18.
Owens, L. D. et al. "A Single Amino Acid Substitution in the Antimicrobial Defense Protein Cecropin B is Associated with Diminished Degradation by Leaf Intercellular Fluid" *MPMI*, 1997, pp. 525-528, vol. 10, No. 4.
Piers, K. L. et al. "Recombinant DNA procedures for producing small antimicrobial cationic peptides in bacteria" *Gene*, 1993, pp. 7-13, vol. 134.
Piers, K.L. et al. "The interaction of a recombinant cecropin/melittin hybrid peptide with the outer membrane of *Pseudomonas aeruginosa*" *Mol Microbiol*, 1994, 12(6):951-958, abstract only.
Piers, K.L. et al. "Improvement of Outer Membrane-Permeabilizing and Lipopolysaccharide-Binding Activities of an Antimicrobial Cationic Peptide by C-Terminal Modification" *Antimicrobial Agents and Chemotherapy*, Oct. 1994, pp. 2311-2316, vol. 38, No. 10.
Sitaram, N. et al. "Interaction of antimicrobial peptides with biological and model membranes: structural and charge requirements for activity" *Biochimica et Biophysica Acta*, 1999, pp. 29-54, vol. 1462.
Steiner, H. et al. "Sequence and specificity of two antibacterial proteins involved in insect immunity" *Nature*, Jul. 16, 1981, pp. 246-248, vol. 292.

(Continued)

*Primary Examiner* — Medina A Ibrahim
*Assistant Examiner* — Jeffrey Bolland
(74) *Attorney, Agent, or Firm* — Saliwanchik, Lloyd & Eisenschenk

(57) ABSTRACT

The subject invention pertains to methods and materials for enhancing microbial resistance in plants. Specifically exemplified herein are grapevines transformed with polynucleotides that express a peptide which confers antimicrobial activity.

31 Claims, 5 Drawing Sheets

(56) References Cited

OTHER PUBLICATIONS

Van Hofsten, P. et al. "Molecular cloning, cDNA sequencing, and chemical synthesis of cecropin B from *Hyalophora cecropia*" *Proc. Natl. Acad. Sci.*, Apr. 1985, pp. 2240-2243, vol. 82.

Varshavsky, A. "The N-end rule: Functions, mysteries, uses" *Proc. Natl. Acad. Sci.*, Oct. 1996, pp. 12142-12149, vol. 93.

Wade, D. et al. "All-D amino acid-containing channel-forming antibiotic peptides" *Proc. Natl. Acad. Sci.*, Jun. 1990, pp. 4761-4795, vol. 87.

* cited by examiner

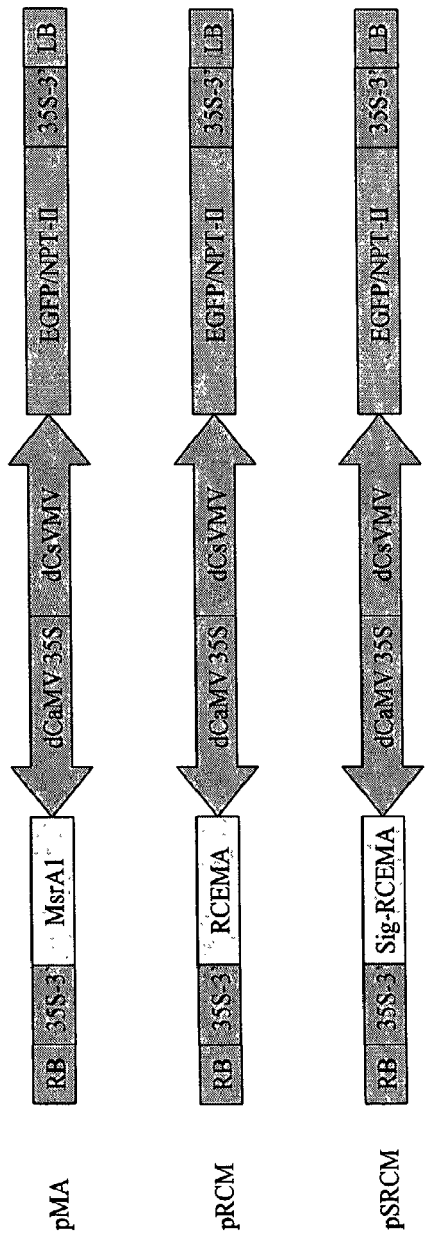
Figure 1. Schematic representation of the T-DNA region of three binary vectors containing lytic peptide and fusion marker genes under control of a bi-directional dual promoter complex Control          RCEMA-transgenic Figure 2. Comparison of a susceptible control plant and a transgenic plant expressing the RCEMA gene three months after inoculation with pathogenic *Xylella fastidiosa* bacterium

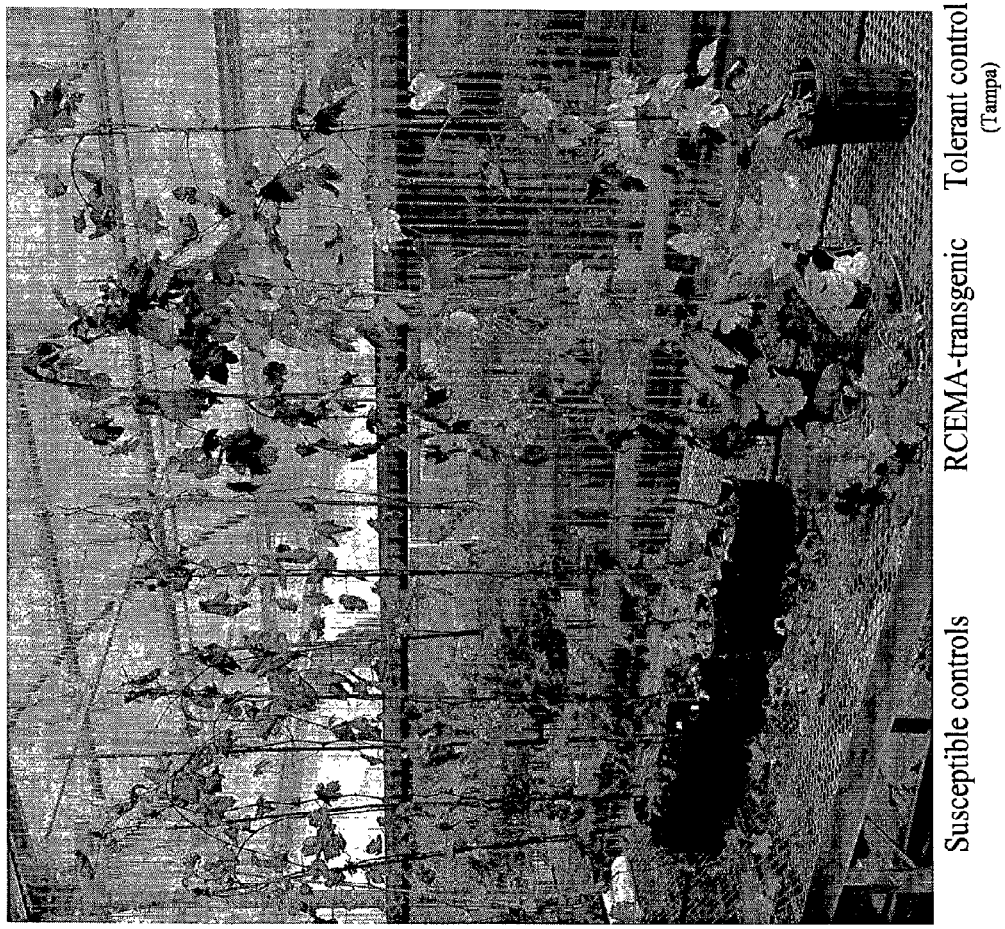
Figure 3. Comparison of susceptible and tolerant control plants and transgenic plants expressing the RCEMA gene six months after disease challenge Figure 4. Re-isolation of *Xylella fastidiosa* bacterium from plant saps of inoculated control and transgenic grape plants expressing the RCEMA gene

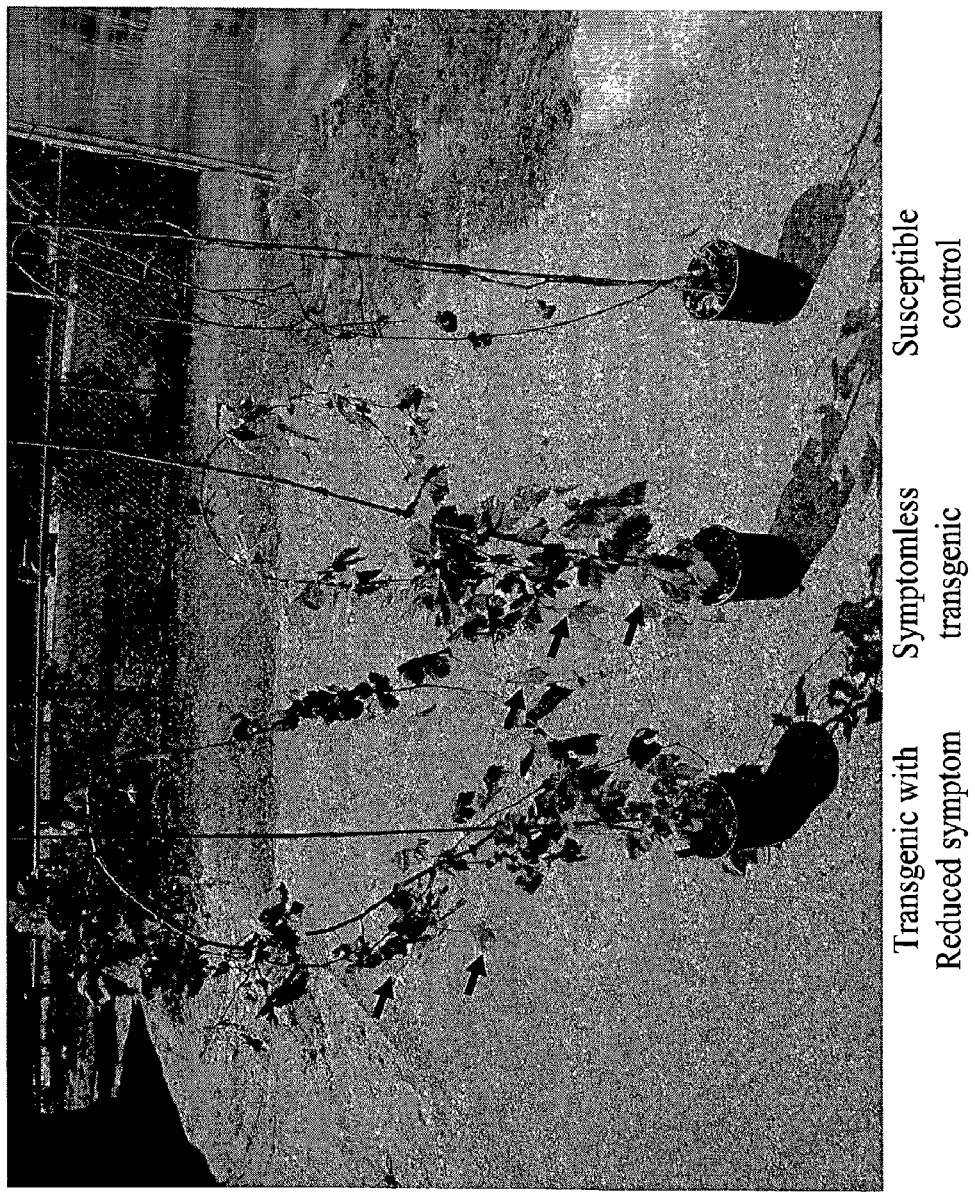
**Figure 5. Production of new shoots from transgenic Thompson Seedless plants expressing the RCEMA gene 8 months after inoculation with *Xylella fastidiosa* bacterium**

ANTIMICROBIAL PEPTIDES AND USES THEREOF

RELATED APPLICATIONS

This application is the U.S. national stage application of International patent application No. PCT/US2006/022935, filed Jun. 13, 2006, which claims priority to U.S. application Ser. No. 60/689,937, filed Jun. 13, 2005, which is incorporated herein by reference in its entirety.

BACKGROUND

In the last two decades, there has been substantial interest in identifying antimicrobial peptides from a variety of donor organisms and exploiting their use for plant protection against both fungal and bacterial pathogens using a transgenic strategy. Among natural lytic peptides, cecropins, melittin and their hybrid chimeras have been tested extensively for their antimicrobial activity.

Cecropins were first found in the hemolyph of pupae of the Hyalophora cecropia silkmoth (Steiner et al. 1981) but subsequently identified from numerous insect species and even from the animal kingdom (Boman and Hultmark 1987; Lee et al. 1989). Structural analyses indicate that cecropins are usually composed of 35-39 amino acid residues with two different domains connected by a flexible non-helical hinge region. The N-terminal domain (head) contains a high proportion of basic amino acids and folds into a perfect amphipathic α-helix, while the C-terminal domain (tail) is rich in hydrophobic residues and forms a more hydrophobic helix (Van Hofsten et al. 1985). The charged N-terminal amphipathic α-helix can easily span a negatively-charged bacterial lipid membrane and exhibit voltage-dependent ion-permeable pore-forming properties (Christensen et al. 1988). Cecropins are potent lytic peptides capable of lysing in vitro a wide variety of Gram-positive and Gram-negative bacteria and play an important role in the humoral immune system in insects without known adverse activity against eukaryotic cells.

Elittin is a 26-residue peptide that constitutes a major toxic component of the venom of European honey bee Apis mellifera (Habermann 1972). Melittin also has a helix-hinge-helix structure similar to that of cecropins but with opposite polarity, i.e. a hydrophobic N terminus and an amphipathic C terminus. The powerful hemolytic and allergenic activity of melittin has precluded any practical use of this peptide as a whole for antimicrobial purposes, nonetheless, its potent antibacterial activity attracted great attention.

Extensive structure-function studies revealed that the amphiphilic helical N-terminal segment (residues 1-14) of melittin possesses channel-forming capability and thus is mostly responsible for antibacterial activity, whereas the hinge region plays a crucial role in modulating hemolytic activity. The C-terminal segment (residues 20 to 26) of melittin had no effect on lytic activity (Sitaram and Nagaraj 1999).

Hybrid peptides composed of various segments of cecropins and melittin have been synthesized and tested in vitro for biological activity against pathogenic bacteria. Based on structural analyses and the concept of α-helix-membrane interactions, Boman et al. (1989) first proposed the use of such hybrid peptides and examined several chemically synthesized hybrid peptides composed of the α-helix regions from different peptides. They found that chimeric peptides containing the amphiphilic 1-13 or 1-8 N-terminal segment of cecropin A and 1-13 or 1-18 region of melittin showed broad-spectrum antimicrobial activity that was up to 100-fold higher than the activity of natural cecropin A. Noticeably, these hybrid peptides, unlike melittin, had low hemolytic activity and did not lyse sheep red blood cells, even at 50-200 times higher concentrations (Boman et al. 1989 and Wade et al. 1990).

Another research group (Piers et al. 1994) subsequently modified the C terminus of a cecropin-melittin hybrid CEME (cecropin 1-8 plus melittin 1-18) that was previously created by Wade et al. (1990) to produce a peptide called CEMA (cecropin 1-8 plus melittin 1-16 plus KLTK). The C-terminal modification with charged residues KLTK in CEMA was suggested to have improved interactions between lytic peptide and lipid membrane or lipid membrane affinity for better outer membrane-permeabilizing capability (Piers et al. 1994). However, various studies by the same group showed that, in spite of the higher in vitro lipid membrane affinity of CEMA, both CEME and CEMA had an essentially identical level of antibacterial activity (Peiers et al. 1994; Gough et al. 1996; Scott et al. 1999) and that CEME also had a high-binding affinity to bacterial lipid membranes and an outstanding outer membrane-permeabilizing capability (Piers and Hancock 1994).

Active natural and synthetic lytic peptides including cecropins and melittin have an amidated C terminus (Wade et al. 1990; Andersonss et al. 1991). The addition of charged residues to the C terminus of CEMA was also suggested to provide a charged environment in recombinant lytic peptides for efficacious interactions with lipid membranes (Piers et al. 1994). However, in a previous study, the same authors demonstrated that recombinant CEME lacking charged C-terminal residues produced by a bacterial expression system had properties (including antibacterial activity) identical to those of chemically synthesized CEME with amidated C terminus (Piers et al. 1993).

Details regarding the design and use of CEMA and related peptides can also be found in several recent US patents by Hancock et al. (U.S. Pat. Nos. 5,593,866; 5,707,855; 6,288,212 and 6,818,407).

Over the years, a variety of lytic peptides have been tested to confer resistance to phytopathogens in transgenic plants. However, the use of genes encoding natural peptides such as cecropins remained to be relatively ineffective and failed to confer any detectable resistance (Hightower et al. 1994; Florack et al. 1995), while genes coding for modified lytic peptides or analogues provided limited enhanced resistance (Arce et al. 1999). Recently, Osusky et al. (2000) reported the obtainment of broad-spectrum resistance in transgenic potato plants by using a variant of CEMA gene, MsrA1. This peptide was modified with a 6-residue (MALEHM) extension at the N terminus of CEMA. The addition of this hexapeptide was postulated to reduce toxicity of peptide products for the host plant. However, constitutive expression of the MsrA1 gene in one of several tested potato genotypes resulted in the non-pathogen-induced "lesion-mimic" morphological changes (Osusky et al. 2000).

BRIEF DESCRIPTION OF THE DRAWINGS

FIG. 1. Schematic representation of the T-DNA region of three binary vectors containing lytic peptide and fusion marker genes under control of a bi-directional duplex promoter complex. RB and LB, right and left borders of T-DNA region; sig, signal peptide fragment from the PR1b gene of tobacco.

FIG. 2. Comparison of a susceptible control plant and a transgenic plant expressing the RCEMA gene three months after inoculation with pathogenic Xylella fastidiosa bacterium. Plants were challenged by injecting two drops of bacterial solution into the main stem at the base region on Jul. 12, 2004. Image was taken on Oct. 17, 2004.

FIG. 3. Comparison of susceptible, tolerant control plants and transgenic plants expressing the RCEMA gene six months after disease challenge. Transgenic plants were challenged twice by injecting two drops of bacterial solution into the main stem at the base region on Jul. 12, 2004 and Nov. 8, 2004, respectively. All control plants were only challenged once. Image was taken on Jan. 1, 2005.

FIG. 4. Re-isolation of *Xylella fastidiosa* bacterium from plant saps of inoculated control and transgenic grape plants. Petioles were collected from individual plants, surface-sterilized with bleach solutions. Plant saps were then extracted from sterilized petiole segments under aseptic condition and plated on culture medium containing nutrients essential for *X. fastidiosa* growth. Cultures were incubated at 28° C. in the dark. Images were taken 8 days after plating. Distance between white grid lines at the bottom of each panel represents 1 mm.

FIG. 5. Production of new shoots from transgenic Thompson Seedless plants expressing the RCEMA gene 8 months after inoculation with *Xylella fastidiosa* bacterium. Plants were inoculated with bacteria on Jul. 12, 2004 and image was recorded on Mar. 5, 2005. Arrows indicate newly produced shoots from challenged transgenic plants.

DETAILED DESCRIPTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

According to one embodiment, the subject invention pertains to a modified cecropin-melittin hybrid peptide that comprises a 2-residue MA extension at the N-terminus. Specifically exemplified are the known CEMA and CEME peptides which comprise a 2-residue MA extension on the N-terminus. Furthermore, another embodiment of the invention is directed to a polynucleotide molecule which encodes such peptides comprising this 2-residue augmentation. As noted above, others have attempted to augment the known CEMA gene by providing a 6-residue extension on the N-terminus, named as the MrsA1 gene, but have observed related undesired effects.

In another embodiment, the subject invention relates to a plant transformed with a polynucleotide that encodes a cecropin-melittin hybrid peptide comprising a MA extension on its N-terminus. Of particular interest is a CEMA or CEME protein comprising an MA extension on its N-terminus.

In a further embodiment, the subject invention pertains to a eukaryotic or prokaryotic cell transformed with a polynucleotide that encodes a hybrid cecropin-melittin hybrid peptide comprising a MA extension on its N-terminus.

The peptide embodiments of the subject invention comprise antimicrobial properties. U.S. Pat. No. 6,288,212 is cited to and incorporated by reference, and describes multiple uses of the peptide embodiments of the subject invention and the polynucleotide molecules that encode them.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

Methods, vectors, and compositions for transforming plants and plant cells in accordance with the invention are well-known to those skilled in the art, and are not particularly limited. For a descriptive example see Karimi et al., TRENDS in Plant Science, Vol. 7, No. 5, May 2002, pp. 193-195, incorporated herein by reference. See also WO 99/059398 and WO 00/0070054

In the context of the present application, a polynucleotide sequence is "homologous" with the sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% or even 95%, 96%, 97%, 98%, and 99%, of which, corresponds to the amino acid sequence SEQ ID NO. 2; wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Variants of known polynucleotide sequences (e.g., those having 80% identity or higher) that code for cecropins or cecropin mellitin hybrid peptides may be identified that also code for peptides possessing antimicrobial properties. In certain embodiments of the subject invention, such variants may be implemented so long as they comprise the additional coding sequence for the 2-residue MA N-terminus.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

A non-exclusive list of examples of plants which may be transformed with certain polynucleotide embodiments includes cereals such as barley, corn, oat, rice, and wheat, melons such as cucumber, muskmelon, and watermelon; legumes such as bean, cowpea, pea, peanut; oil crops such as canola and soybean; solanaceous plants such as tobacco, tuber crops such as potato and sweet potato, and vegetables like tomato, pepper and radish; fruits such as pear, grape, peach, plum, banana, apple, and strawberry; fiber crops like the Gossypium genus such as cotton, flax and hemp; and other plants such as beet, cotton, coffee, radish, commercial flowering plants, such as carnation and roses; grasses, such as sugar cane or turfgrass; evergreen trees such as fir, spruce, and pine, and deciduous trees, such as maple and oak. Of particular present interest is grape, *Vitis vinifera*.

Example 1

The inventors have discovered that the 2-residue peptide possesses an unexpected enhanced microbial activity. In order to develop resistance against *Xylella fastidiosa*, the causal agent for Pierce's disease (PD) in grape (*Vitis vinifera*) using transgenic technology, we introduced several previously reported lytic peptide genes, including the MsrA1 gene and a number of modified CEMA derivatives and examined their biological activity in transgenic grape plants. Here we disclosed that a grape codon-optimized gene called RCEMA under the control of a bi-directional duplex promoter complex (Li et al. 2004) provided strong resistance to *X. fastidiosa* under stringent in vivo test conditions, while the MsrA1 gene failed to provide similar level of resistance. The RCEMA gene (named for CEMA with a reduced-extension) encodes a CEMA peptide chimera with a 2-residue (MA) extension at the N terminus. Transgenic grape plants expressing the RCEMA gene are able to survive repeated inoculations with pathogenic *X. fastidiosa* bacterium without or with lessened visible symptoms for over 8 months and produced morphological characteristics identical to non-transformed grape plants. Under the same stringent test conditions, susceptible control plants developed severe PD symptoms and died within a time period of 8-10 weeks. Furthermore, plant saps extracted from a large number of resistant RCEMA-transgenic plants produced no or a significantly reduced number of bacterial colonies after culture on *X. fastidiosa*-specific culture medium when compared with plant saps from susceptible and tolerant control plants. The newly developed RCEMA gene provides an excellent candidate for the development of sustainable PD resistance in otherwise susceptible *V. vinifera* grape cultivars and facilitates the advancement of viticulture and wine industry in PD-affected areas.

a. Construction of Lytic Peptide Genes and Transformation Vectors

The MsrA1 and RCEMA peptides contain 34 (MALEHMKWKLFKKIGIG AVLKVLTTGLPALKLTK) (SEQ ID NO. 1) and 30 (MAKWKLFKKIGIGA VLKVLTTGLPALKLTK) (SEQ ID NO. 2) amino acid residues, respectively. Double stranded DNA sequences coding for MsrA1 and RCEMA were synthesized by ligation of chemically synthesized oligonucleotide primers. In designing the DNA sequences, codons preferably used by *V. vinifera* species were chosen to encode each amino acid residue at the DNA level (see codon usage table for *V vinifera* from http:// www.kazusa.or.jp/codon/cgi-bin/showcodon.cgi?species=Vitis+vinifera+[gbpln]). Both genes were subsequently cloned into a pUC-19 plasmid vector and nucleotide sequences were confirmed by DNA sequencing.

Both MsrA1 and RCEMA genes were subcloned into an expression cassette under control of a constitutive double enhanced CaMV 35S promoter and subsequently introduced into a binary vector pDCsVM that contained a fusion EGFP/NPT-II marker gene expression unit (Li et al. 2001), resulting in transformation vector pMA and pRCM, respectively. In addition, a variant binary vector pSRCM was also constructed in which a signal peptide sequence from the PR1b gene of tobacco was incorporated at the N-terminus of RCEMA gene (FIG. 1). In these vectors, all lytic peptide gene expression units were placed in a divergent orientation with the double enhanced promoter complex that controls the expression of the fusion marker gene, thus forming a bi-directional duplex promoter complex (BDPC) for the expression of both peptide and fusion marker genes. BDPC has been shown to be capable of conferring a significantly enhanced level of gene expression for associated transgenes in transgenic plants (Li et al. 2004).

All binary vectors were introduced into Agrobacterium tumefaciens strain EHA105 and then used in subsequent transformation experiments.

b. Agrobacterium-Mediated Transformation and Recovery of Transgenic Grape Plants Transgenic grape plants of Thompson Seedless containing above-mentioned lytic peptide genes were obtained after Agrobacterium-mediated transformation of grape SE using a previously described procedure with modifications (Li et al. 2001). Thompson Seedless was used due to its high transformation efficiencies that we obtained routinely in our laboratory. Thompson Seedless, as in the case of all other V. vinifera cultivars, is a highly susceptible cultivar to PD, thus providing an excellent model for identifying PD resistance. Over one thousand transgenic plants have been regenerated thus far and most of them successfully established in the greenhouse for in vivo testing. All transgenic plants showed normal transgene expression based on the visualization of GFP-specific fluorescence derived from the expression of the EGFP-NPT-II fusion marker gene (Li et al. 2001).

c. Confirmation of Resistance to Xylella fastidiosa from Lytic Peptide Chimeras Via Greenhouse Test Transgenic plants that had been grown in the greenhouse for about one month were inoculated with pathogenic X. fastidiosa bacterium by injecting two drops (30 µl) of bacterial solution ($OD_{600}$ value=0.2 or a titer of $1 \times 10^7$ cfu/ml) into the main stem at the base region. Plants were continuously maintained in the greenhouse under normal growth condition. About six weeks after inoculation, plants were monitored for the development of PD symptoms that resemble marginal burns on affected leaves throughout the plant. PD-susceptible plants died in the next few weeks as a result of colonization and severe clogging of xylem systems by X. fastidiosa bacterium that eventually lead to the loss of all viable leaves (FIG. 2, control plants).

Since early July of 2004, up to seven inoculation experiments have been conducted to test hundreds of independent transgenic plant lines and control plants. In these experiments all susceptible control plants died within a time period of 8-10 weeks. Furthermore, all plants of PD-tolerant control cultivar Tampa also developed severe PD symptoms and some died eventually due to progressive disease development, indicating the high degree of stringency of our test conditions (FIG. 2).

From numerous tested lines of transgenic plants expressing the MsrA1 gene, only one survived but with pronounced PD symptoms. However, a relatively high number of X. fastidiosa bacterial colonies subsequently were recovered from the plant sap isolated from this particular plant (Table 1). On the other hand, a large number of symptomless plants and plants with lessened PD symptoms were identified from independent transgenic lines expressing either the RCEMA or the Sig-RCEMA genes (FIGS. 2 and 3). Some of these resistant plants remained symptomless for over 8 month even with repeated inoculations with X. fastidiosa bacterium (FIG. 3). Bacterial isolation experiments using plant saps and PD bacterium-specific culture medium indicated that most of these resistant plants gave rise to significantly reduced bacterial colony formation as compared to control plants, while some symptomless plants yielded a few or no bacterial colonies (FIG. 4, Table 1). At this time (early spring of 2005 and up to 8 months after inoculation with active PD pathogen), resistant plants successfully produced healthy, robust new shoots (FIG. 5). The significant reduction and/or disappearance of introduced X. fastidiosa bacteria within the plant system and the normal plant growth after a stringent disease challenge strongly confirmed the correlation between the expression of the RCEMA or Sig-RCEMA genes and the significant impediment of bacterial propagation and colonization within the xylem system in these resistant transgenic plants.

We have introduced the MsrA1 gene previously reported by Osusky et al. (2000) into transgenic grape plants as a positive control in experiments designed to evaluate a series of lytic peptide candidates in an effort to develop an efficacious strategy to tackle PD problems in grape by using transgenic technology. However, this gene showed no significant resistance to the xylem-limited bacterium X. fastidiosa. All transgenic plants expressing the MsrA1 gene eventually succumbed to the high disease pressure in our stringent greenhouse test and died, except for one plant line that did show reduced PD symptoms but with a high level of in vivo bacterial propagation. Our finding is in complete disagreement with the previous report by Osusky et al. (2000) where high levels of antimicrobial activity and disease resistance were obtained in transgenic potato against several systemic bacterial and fungal pathogens. The inability of this gene to confer resistance to X fastidiosa in transgenic grape may be attributed to the reduced level of antibacterial activity due to the use of hexapeptide extension (Osusky et al. 2000) and the instability of the peptide molecule in xylem environment where X. fastidiosa only resides due to the incorporation of several destabilizing amino acid residues including L, E and H within the N-terminal extension (Varshavsky 1996).

To our knowledge, the direct use of recombinant CEME or CEMA peptides in transgenic plants to confer successful resistance to phytopathogens has not been reported. In addition, over the course of more than two decades numerous attempts to express natural cecropins or related peptides in transgenic plants also failed to give rise to any tangible disease resistance in plants. One common structural feature of these natural peptide molecules is that they all have a highly destabilizing amino acid residue K at the N terminus. The presence of a destabilizing N-end residue, according to the N-end rule, renders these peptides highly susceptible to rapid protein degradation in all living organisms (Varshavsky 1996). Therefore, the high degree of in vivo instability prevented the expected level of accumulation of these peptides in plant cells that is required to fend off phytopathogens, and precluded their practical use for the development of disease resistance in trangenic plants (Owens and Heutte 1997).

We developed a peptide chimera RCEMA composed of only a 2-residue extension (MA) at the N terminus of the CEMA and showed that this peptide chimera when produced at high levels under the control of a highly efficient bi-directional duplex promoter complex is capable of conferring strong resistance to the xylem-limited bacterium *X. fastidiosa* in transgenic grape plants. A large number of transgenic plants challenged under highly stringent testing conditions produced no and/or significantly lessened disease symptoms. Culture of plant saps on *X. fastidiosa*-specific medium revealed that symptomless plants produced no bacterial colonies, while plants with significantly lessened symptoms yielded substantially reduced number of bacterial colonies as compared to susceptible control plants. Our findings indicate that a 2-residue (MA) N-terminal extension containing a stabilizing residue A provides a better in vivo stability for the RCEMA peptide molecules, in contrast to the case of MsrA1 in which several destabilizing N-terminal residues were incorporated (Piers et al. 1994). The short N-terminal extension of the RCEMA peptide also ensures the retainment of a high level of antimicrobial activity against bacterial pathogens in variegated tissues, including xylem environment. Accordingly, the RCEMA gene provides an excellent candidate for the development of sustainable resistance to PD in grape and other diseases in crop plants.

REFERENCES

Andersons D, Engstrom A, Josephson S, Hansson L and Steiner H (1991) Biologically active and amidated cecropin produced in a baculovirus expression system from a fusion construct containing the antibody-binding part of protein A. Biochem J 280:219-224.

Boman H G and Hultmark D (1987) Cell-free immunity in insects. Annu Rev Microbiol. 41:103-26.

Boman H G, Wade D, Boman I A, Wahlin B and Merrifield (1989) Antibacterial and antimalarial properties of peptides that are cecropin-melittin hybrids. FEBS Lett 259: 103-106.

Christensen B, Fink J, Merrifield R B and Mauzerall D (1988) Channel-forming properties of cecropins and related model compounds incorporated into planar lipid membranes. PNAS 85:5072-5076.

Florack D, Allefs S, Bollen R, Basch D, Visser B and Stiekema W (1995) Expression of giant silkmoth cecropin B genes in tobacco. Transgenic Res 4:132-141.

Gough M, Hancock R E W and Kelly N M (1996) Antiendotoxin activity of cationic peptide antimicrobial agents. Infection and Immunity 64:4922-4927.

Hanbermann E (1972) Bee and wasp venoms. Science 177: 314-22.

Hightower R, Baden C, Penzes E and Dunsmuir P (1994) The expression of cecropin peptide in transgenic tobacco does not confer resistance to *Pseudomonas syringae* pv *tabaci*. Plant Cell Rep 13:295-299.

Lee J Y, Boman A, Sun C, Andersson M, Jornvall H, Mutt V and Boman H G (1989) Antibacterial peptides from pig intestine: isolation of a mammalian cecropin. PNAS 86:9159-9162.

Li Z T, Jayasankar S and Gray D J (2001) Expression of a bifunctional green fluorescent protein (GFP) fusion marker under the control of three constitutive promoters and enhanced derivatives in transgenic grape (*Vitis vinifera*). Plant Sci 160:877-887.

Li Z T, Jayasankar S and Gray D J (2004) Bi-directional duplex promoters with duplicated enhancers significantly increase transgene expression in grape and tobacco. Transgenic Res 13:143-154.

Owens L D and Heutte T M (1997) A single amino acid substitution in the antimicrobial defense protein cecropin B is associated with diminished degradation by leaf intercellular fluid. Mol Plant-Microbe Inter 10:525-528.

Piers K L, Brown M B and Hancock R E W (1993) Recombinant DNA procedures for producing small antimicrobial cationic peptides in bacteria. Gene 134:7-13.

Piers K L and Hancock R E (1994) The interaction of a recombinant cecropin/melittin hybrid peptide with the outer membrane of Pseudomonas aeruginosa. Molecular Microbiology 12:951-8.

Piers K L, Brown M H and Hancock R E W (1994) Improvement of outer membrane-permeabilizing and lipopolysaccharide-binding activities of an antimicrobial cationic peptide by C-terminal modification. Antimicro Agents Chemother 38:2311-2316.

Osusky M, Zhou G, Osuska L, Hancock R E W, Kay W W and Misra S (2000) Transgenic plants expressing cationic peptide chimeras exhibit broad-spectrum resistance to phytopathogens. Nature Biotechn 18:1162-1166.

Sitaram N and Nagaraj R (1999) Interaction of antimicrobial peptides with biological and model membranes: structure and charge requirements for activity. Biochem Biophys Acta 1462:29-54.

Steiner H, Hultmark D, Engstrom A, Bennich H, Boman H G (1981) Sequence and specificity of two antibacterial proteins involved in insect immunity. Nature 292:246-8.

Van Hofsten P, Faye I, Kockum K, Lee J-Y, Xanthopoulos K G, Boman I A, Boman H G, Engstrom A, Andreu D and Merrifield R B (1985) Molecular cloning, cDNA sequencing, and chemical synthesis of cecropin B from *Hyalophora cecropia*. PNAS 1985 82: 2240-2243.

Wade D, Boman A, Wahlin B, Drain C M, Andreu D, Boman H G and Merrifield R B (1990) All-D amino acid-containing channel-forming antibiotic peptides. PNAS 87:4761-4765.

Varshavsky A (1996) The N-end rule: functions, mysteries, uses. PNAS 93:12142-12149.

C. Cited Patents

Hancock R E W, Piers K L, Brown M H. (1997) Cationic peptides and method for production. U.S. Pat. No. 5,593,866.

Hancock R E W, Piers K L, Brown M H. (1998) CEMA cationic peptide and polynucleotides coding CEMA. U.S. Pat. No. 5,707,855

Hancock R E W, Gough M A, Patrzykat A, Woods D, Jia A (2001) Anti-endotoxic, antimicrobial cationic peptides and methods of use thereof. U.S. Pat. No. 6,288,212.

Hancock R E W, Gough M A, Patrzykat A, Woods D, Jia A (2004) Anti-endotoxic, antimicrobial cationic peptides and methods of use thereof. U.S. Pat. No. 6,818,407.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference in their entirety to the extent they are not inconsistent with the teachings herein.

What is claimed is:

1. A polynucleotide molecule comprising a nucleotide sequence that encodes a hybrid polypeptide comprising the amino acid sequence of SEQ ID NO: 2, or having at least 95% sequence identity with SEQ ID NO: 2, wherein said polypeptide exhibits antimicrobial activity.

2. A plant transformed to express a polynucleotide molecule comprising a nucleotide sequence that encodes a hybrid polypeptide comprising the amino acid sequence of SEQ ID NO: 2, or having at least 95% sequence identity with SEQ ID NO: 2, wherein said polypeptide exhibits antimicrobial activity.

3. The plant of claim 2, wherein said plant is barley, corn, oat, rice, wheat, cucumber, muskmelon, watermelon, bean, cowpea, pea, peanut, canola, soybean, tobacco, potato, sweet potato, tomato, pepper, radish, pear, grape, peach, plum, banana, apple, citrus, strawberry, cotton, flax, hemp, beet, cotton, coffee, or radish.

4. The plant of claim 2, wherein said plant is *Vitis vinerfera*.

5. A eukaryotic or prokaryotic cell transformed with a polynucleotide molecule comprising a nucleotide sequence that encodes a hybrid polypeptide comprising the amino acid sequence of SEQ ID NO: 2, or having at least 95% sequence identity with SEQ ID NO: 2, wherein said polypeptide exhibits antimicrobial activity.

6. A method for increasing antimicrobial activity in a plant comprising:
obtaining a polynucleotide molecule comprising a nucleotide sequence that encodes a hybrid polypeptide comprising the amino acid sequence of SEQ ID NO: 2, or having at least 95% sequence identity with SEQ ID NO: 2, wherein said polypeptide exhibits antimicrobial activity; and
introducing said polynucleotide molecule into a plant cell to achieve a transformed plant cell.

7. The method of claim 6, further comprising regenerating a plant from said transformed plant cell.

8. The method of claim 6, wherein said plant is barley, corn, oat, rice, wheat, cucumber, muskmelon, watermelon, bean, cowpea, pea, peanut, canola, soybean, tobacco, potato, sweet potato, tomato, pepper, radish, pear, grape, peach, plum, banana, apple, citrus, strawberry, cotton, flax, hemp, beet, cotton, coffee, or radish.

9. The method of claim 6, wherein said plant is *Vitis vinifera*.

10. The cell of claim 5, wherein said cell is a plant cell.

11. The plant of claim 2, wherein said plant is a cereal, melon, legume, oil crop, solanaceous plant, tuber, vegetable, fruit, fiber crop, flowering plant, grass, evergreen tree, or deciduous tree.

12. The method of claim 6, wherein said plant is a cereal, melon, legume, oil crop, solanaceous plant, tuber, vegetable, fruit, fiber crop, flowering plant, grass, evergreen tree, or deciduous tree.

13. The method of claim 6, wherein said nucleotide sequence is codon-optimized for expression in *Vitis vinifera*.

14. The method of claim 6, wherein said polynucleotide comprises an expression cassette for expressing said nucleotide sequence.

15. The polynucleotide of claim 1, wherein said polypeptide consists of the amino acid sequence of SEQ ID NO:2.

16. The plant of claim 2, wherein said polypeptide consists of the amino acid sequence of SEQ ID NO:2.

17. The cell of claim 5, wherein said polypeptide consists of the amino acid sequence of SEQ ID NO:2.

18. The method of claim 6, wherein said polypeptide consists of the amino acid sequence of SEQ ID NO:2.

19. The polynucleotide of claim 1, wherein said nucleotide sequence is codon-optimized for expression in *Vitis vinifera*.

20. The plant of claim 4, wherein said nucleotide sequence is codon-optimized for expression in *Vitis vinifera*.

21. The polynucleotide of claim 1, wherein said polynucleotide comprises an expression cassette for expressing said nucleotide sequence.

22. The polynucleotide of claim 1, wherein said antimicrobial activity is against *Xylella fastidiosa*.

23. The plant of claim 1, wherein said antimicrobial activity is against *Xylella fastidiosa*.

24. The method of claim 6, wherein said antimicrobial activity is against *Xylella fastidiosa*.

25. The polynucleotide of claim 1, wherein said polypeptide comprises amino acids methionine (M) and alanine (A) at the N-terminus of said polypeptide.

26. The plant of claim 2, wherein said polypeptide comprises amino acids methionine (M) and alanine (A) at the N-terminus of said polypeptide.

27. The cell of claim 5, wherein said polypeptide comprises amino acids methionine (M) and alanine (A) at the N-terminus of said polypeptide.

28. The method of claim 6, wherein said polypeptide comprises amino acids methionine (M) and alanine (A) at the N-terminus of said polypeptide.

29. The plant of claim 2, wherein said plant is a citrus plant.

30. The method of claim 6, wherein said plant is a citrus plant.

31. An isolated vector comprising the polynucleotide of claim 1.

* * * * *

UNITED STATES PATENT AND TRADEMARK OFFICE
CERTIFICATE OF CORRECTION

PATENT NO. : 8,592,651 B2  
APPLICATION NO. : 11/922048  
DATED : November 26, 2013  
INVENTOR(S) : Zhijian T. Li et al.

Page 1 of 1

It is certified that error appears in the above-identified patent and that said Letters Patent is hereby corrected as shown below:

In the Specification

Column 2,
Line 24, "Andersonss" should read --Andersons--

Column 3,
Line 64, "MrsA1" should read --MsrA1--

Column 4,
Line 26, "WO 00/0070054" should read --WO 00/070054.--

In the Claims

Column 11,
Line 54, "vinerfera" should read --vinifera--

Signed and Sealed this
Fifteenth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,592,651 B2  Page 1 of 1
APPLICATION NO. : 11/922048
DATED : November 26, 2013
INVENTOR(S) : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1625 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 34
<212> TYPE: PRT
<213> ORGANISM: Artificial Sequence
<220> FEATURE:
<223> OTHER INFORMATION: modified cecropin-melittin hybrid peptide
      designated as MsrA1 peptide

<400> SEQUENCE: 1

Met Ala Leu Glu His Met Lys Trp Lys Leu Phe Lys Lys Ile Gly Ile
1               5                   10                  15

Gly Ala Val Leu Lys Val Leu Thr Thr Gly Leu Pro Ala Leu Lys Leu
            20                  25                  30

Thr Leu

<210> SEQ ID NO 2
<211> LENGTH: 30
<212> TYPE: PRT
<213> ORGANISM: Artificial Sequence
<220> FEATURE:
<223> OTHER INFORMATION: modified cecropin-melittin hybrid peptide
      designated as RCEMA peptide

<400> SEQUENCE: 2

Met Ala Lys Trp Lys Leu Phe Lys Lys Ile Gly Ile Gly Ala Val Leu
1               5                   10                  15

Lys Val Leu Thr Thr Gly Leu Pro Ala Leu Lys Leu Thr Lys
            20                  25                  30
```